United States Patent [19]

Whittle

[11] Patent Number: 4,788,297

[45] Date of Patent: Nov. 29, 1988

[54] SEPARATION OF ISOMERS

[75] Inventor: Alan J. Whittle, Aldershot, England

[73] Assignee: Imperial Chemical Industries PLC, London, England

[21] Appl. No.: 769,492

[22] Filed: Aug. 26, 1985

[51] Int. Cl.$^4$ ............................................ C07D 311/56
[52] U.S. Cl. ..................................... 549/285; 549/286
[58] Field of Search ................................ 549/285, 286

[56] References Cited

U.S. PATENT DOCUMENTS 4,035,505 7/1977 Hadler et al. ........................ 549/286

FOREIGN PATENT DOCUMENTS 2126578 6/1983 United Kingdom ................... 546/85

OTHER PUBLICATIONS

Weissberger, A. Separation and Purification vol. III part I p. 396–398.
Robertson, G. R. Laboratory Practice of Organic Chemistry 3rd Ed. p. 178.
Eliel, E. L. Stereochemistry of carbon compounds 1962, p. 325–329.
Wilen, S. H. Enantiomers, Racemates and Resolutions, pp. 238 and 239.

Primary Examiner—Mary C. Lee
Assistant Examiner—Johann Richter
Attorney, Agent, or Firm—Cushman, Darby & Cushman

[57] ABSTRACT

Process for selective removal of the cis-isomer and consequent enrichment of a solution with respect to the trans-isomer of a 1-(4-hydroxycoumarin-3-yl)-3-substituted phenyl)tetrahydronaphthalene rodenticide by crystallization from hot solvent.

4 Claims, No Drawings

SEPARATION OF ISOMERS

This invention relates to cis and trans isomers of disubstituted tetrahydronaphthalene derivatives. More particularly, it relates to separation of cis and trans isomeric forms of 4-hydroxycoumarin-3-yl substituted tetrahydronaphthalene derivatives useful as rodenticides.

The preparation of a compound which may be named as 1-(4-hydroxycoumarin-2-yl)-3-[4-(4-trifluoromethylbenzyloxy)phenyl]-1,2,3,4-tetrahydronaphthalene is described in GB-A- No. 2126578. The compound is said to be a mixture or cis and trans isomers (hereinafter called "the cis/trans mixture"). The melting point is given as 85°–86° C. but on repeating the preparation of this compound we have found that the product is produced in the form of a viscous oil containing a substantially 1:1 mixture of the cis and trans isomers. This could not be induced to crystallise directly, but we have devised a technique for crystallising out a substantially cis product, and thereby also obtaining a product substantially enriched with respect to the trans-isomers. It is desirable to have a technique to separate the isomers because although cis and trans isomers have substantially similar rodenticial properties the trans-isomers appear to be more rapidly metabolised by scavenging animals and are therefore less hazardous to, for example, birds, foxes, cats and the like which may feed on the carcases of poisoned rodents.

The technique is believed to be applicable not only to the above compound but also to other related 3-substituted-1-(4-hydroxycoumarin-3-yl)-1,2,3,4-tetrahydronaphthalenes active as rodenticides, such as those described in U.S. Pat. No. 4035505 and British Patent Application No. 2126578. Typical 3-substituents include 4-trifluoromethylphenyl, 4'-trifluoromethylbiphenyl-4-yl, 4'-bromobiphenyl-4-yl, 4'-cyanobiphenyl-4-yl and biphenyl-4-yl.

Accordingly, the present invention provides a method for the selective removal of the cis-isomer and the relative enrichment of a 3-substituent-1-(4-hydroxycoumarin-3-yl)-1,2,3,4-tetrahydronaphthalene rodenticide with respect to the trans-isomer which comprises the steps of:

(a) dissolving a quantity of the cis/trans mixture in just sufficient of a heated lower alkanol containing up to four carbon atoms to effect solution, (b) allowing the solution to cool to a temperature within the range which is less than the temperature at which solution occurs but above the ambient temperature, (c) maintaining the solution temperature within this range whilst precipitation of the cis-isomer occurs, (d) separating the precipitated cis-isomer from the solution, and (e) recovering a product enriched with respect to the trans-isomer from the solution.

A preferred alkanol is ethanol. In step (a) of the process the alkanol is preferably heated to a temperature at or just below the boiling point. Thus for ethanol the preferred temperature is within the range 60°–78° C.

In steps (b) and (c) the temperature is preferably within the range from about 32° to about 45° C.

The cis-isomer recovered in step (d) may be contaminated with up to 10% of the trans-isomer. In the case of the compound 1-(4-hydroxycoumarin-3-yl)-3-[4-(4trifluoromethylbenzyloxy)phenyl]-1,2,3,4-tetrahydronaphthalene (Compound A) it is characterised by a melting point within the range from about 170° to about 190° C. A product containing 95% of the cis-isomer and 5% of the trans-isomer has a melting point within the range 183° to 184.5° C. It will be noted that this is significantly different from the melting point of 85–86° C. quoted in GB-A-No. 2126578 for the cis/trans mixture.

The success of the process is surprising in view of the fact that when the cis/trans mixture of Compound A is dissolved in cold ethanol (at or below the ambient temperature) and the solvent is permitted to evaporate at the ambient temperature, the product which crystallises out is the trans-isomer rather than the cis-isomer. The trans-isomer of Compound A has a melting point within the range from about 140° to about 160° C. depending upon the amount of cis-isomer present. Thus a product consisting of 93% of the trans-isomer and 7% of the cis-isomer melts at 153° to 155° C.; significantly higher than the quoted melting point for the cis/trans mixture.

In a further aspect therefore the present invention provides (a) the substantially pure cis-isomer of Compound A characterised in that it has a melting point within the range from about 170° to about 190° C., and contains less than 10% of the trans-isomer, and (b) the substantially pure trans-isomer of Compound A characterised in that it has a melting point within the range from about 140° to about 160° C., and contains less than 10% of the cis-isomer.

The following Example illustrates the invention.

EXAMPLE 1

An approximately 1:1 mixture of the cis and trans isomers of 1-(4-hydroxycoumarin-3-yl)-3-[4-(4-trifluoromethylbenzyloxy)phenyl]-1,2,3,4-tetrahydronaphthalene in the form of a viscous oil (13.0g) was dissolved in ethanol (250 cm$^3$) at the ambient temperature and the solution kept in an open flask at the ambient temperature for 3 days during which time some of the ethanol evaporated and some precipitation of a solid material occurred. This was collected by filtration and dried to give trans-(4-hydroxycoumarin-3-yl)-3-[4-(4-trifluoromethylbenzyloxy)phenyl]-1,2,3,4-tetrahydronaphthalene (containing 7% by weight of the cis-isomer, 1.5g), melting point 153°–155° C. The filtrate was concentrated by removal of the ethanol by evaporation under reduced pressure. The residual oil was then dissolved in boiling ethanol (100cm$^3$) and the solution allowed to cool to 35° to 40° C. and maintained at this temperature whilst a precipitate formed rapidly. This was collected by filtration and dried to give cis-1-(4-hydroxycoumarin-3-yl) -3-[4-(4-trifluoromethylbenzyloxy)phenyl]1,2,3,4-tetra-hydronaphthalene (containing 5% by weight of the trans-isomer, 5.5g) melting point 183°–184° C.

The residue obtained from the filtrate was eluted through a silica column (using chloroform as eluent) to give a product (3.3g) containing 85% of the trans-isomer and 15% of the cis-isomer.

I claim:

1. A process for the selective removal of the cis-isomer and the relative enrichment of a 3-substituted-1-(4-hydroxycoumarin-3-yl)-1,2,3,4-tetrahydronaphthalene rodenticide with respect to the trans-isomer which comprises the steps of:

(a) dissolving a quantity of a cis/trans mixture of said rodenticide in just sufficient of a heated lower alkanol containing up to four carbon atoms to effect solution, (b) allowing the solution to cool to a temperature within the range which is less than the temperature at which solution occurs but above the ambient temperature, (c) maintaining the solution temperature within this range whilst precipitation of the cis-isomer occurs, (d) separating the precipitated cis-isomer from the solution, and (e) recovering a product enriched with respect to the trans-isomer from the solution.

2. The process according to claim 1 wherein the alkanol is ethanol.

3. The process according to claim 1 wherein in step (a) the alkanol is heated to a temperature at or just below the boiling point.

4. The process according to claim 1 wherein the temperature of the solution in step (b) and step (c) is maintained within the range 32° to 45° C.

* * * * *